(12) United States Patent
Lewis et al.

(10) Patent No.: US 6,773,671 B1
(45) Date of Patent: Aug. 10, 2004

(54) MULTICHEMISTRY MEASURING DEVICE AND TEST STRIPS

(75) Inventors: Mark E. Lewis, Groton, MA (US); Geoffrey R. Chambers, Northwood (GB); Marshall D. Deweese, Newton, MA (US); William H. Ames, Holden, MA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/441,674

(22) Filed: Nov. 17, 1999

Related U.S. Application Data (60) Provisional application No. 60/110,331, filed on Nov. 30, 1998.

(51) Int. Cl.[7] .................. G01N 33/48; G01N 31/00
(52) U.S. Cl. .................. 422/58; 422/56; 422/61; 422/82.01; 422/169; 422/170; 422/174
(58) Field of Search .................. 422/58, 56, 82.01, 422/61, 169, 170, 174

(56) References Cited

U.S. PATENT DOCUMENTS

| | | | |
|---|---|---|---|
| 4,065,263 A | 12/1977 | Woodbridge, III | 422/61 |
| 4,297,569 A | 10/1981 | Flies | 235/445 |
| 4,329,642 A | 5/1982 | Luthi et al. | 324/158 |
| 4,545,382 A | 10/1985 | Higgins et al. | 128/635 |
| 4,552,458 A | 11/1985 | Lowne | 356/446 |
| 4,648,665 A | 3/1987 | Davis et al. | 422/56 |
| 4,711,245 A | 12/1987 | Higgins et al. | 128/635 |
| 4,806,311 A | 2/1989 | Greenquist | 422/56 |
| 4,806,312 A | 2/1989 | Greenquist | 422/56 |
| 4,810,203 A | 3/1989 | Komatsu | 422/61 |
| 4,820,636 A | 4/1989 | Hill et al. | 435/14 |
| 4,864,229 A | 9/1989 | Lauks et al. | |
| 4,938,860 A | 7/1990 | Wogoman | 422/61 |
| 4,954,087 A | 9/1990 | Lauks et al. | 435/14 |
| 4,993,048 A | 2/1991 | Williams et al. | |
| 5,008,616 A | 4/1991 | Lauks et al. | |
| 5,039,618 A | 8/1991 | Stone | 436/77 |
| 5,053,199 A | 10/1991 | Keiser et al. | 422/68.1 |

(List continued on next page.)

FOREIGN PATENT DOCUMENTS

| | | |
|---|---|---|
| EP | 0 006 031 | 12/1979 |
| EP | 0 351 891 | 1/1990 |
| EP | 0 377 503 | 7/1990 |
| EP | 0 567 067 | 10/1993 |
| EP | 0 837 320 | 4/1998 |
| EP | 0 840 122 | 5/1998 |
| GB | 2 254 436 | 10/1992 |
| WO | 96/13707 | 5/1996 |
| WO | 98/05424 | 2/1998 |

OTHER PUBLICATIONS i—Stat Product Brochure, i—Stat Corporation, East Windsor, NJ 08520, 1993.

*Primary Examiner*—Jill Warden
*Assistant Examiner*—LaToya I. Cross
(74) *Attorney, Agent, or Firm*—David L. Weinstein (57) ABSTRACT

A multichemistry measuring device and diagnostic test strips which, in combination with the multichemistry measuring device, provide a multichemistry testing system are disclosed. The test strips are for chemical analysis of a sample, and are adapted for use in combination with a measuring device having a test port and capable of performing a multiplicity of testing functionalities. Each type of test strip corresponds to at least one of the testing functionalities, and at least some types of test strips have indicators of the testing functionality on them. The test port is adapted for use in combination with a multiplicity of different types of test strips and includes a sensor capable of specifically interacting with the indicator(s) on the test strips, thereby selecting at least one of the multiplicity of testing functionalities corresponding to the type of test strip.

58 Claims, 4 Drawing Sheets

U.S. PATENT DOCUMENTS

| | | |
|---|---|---|
| 5,096,669 A | 3/1992 | Lauks et al. |
| 5,141,850 A | 8/1992 | Cole et al. .................. 436/525 |
| 5,182,707 A | 1/1993 | Cooper et al. ......... 364/413.11 |
| 5,200,051 A | 4/1993 | Cozzette et al. |
| 5,212,050 A | 5/1993 | Mier et al. |
| 5,234,813 A | 8/1993 | McGeehan et al. .......... 435/7.9 |
| 5,281,395 A | 1/1994 | Markart et al. .......... 422/82.05 |
| 5,312,590 A | 5/1994 | Gunasingham .............. 422/56 |
| 5,366,609 A | 11/1994 | White et al. ................ 204/423 |
| 5,376,254 A | 12/1994 | Fisher ....................... 204/416 |
| 5,395,504 A | 3/1995 | Saurer et al. ............... 204/463 |
| 5,447,837 A | 9/1995 | Urnovitz ....................... 435/5 |
| 5,477,326 A | 12/1995 | Dosmann ................... 356/406 |
| 5,500,350 A | 3/1996 | Baker et al. .............. 435/7.92 |
| 5,508,200 A | 4/1996 | Tiffany et al. ................ 436/44 |
| 5,509,410 A | 4/1996 | Hill et al. ................... 128/637 |
| 5,532,128 A | 7/1996 | Eggers et al. ................. 435/16 |
| 5,556,789 A | 9/1996 | Goerlach-Graw et al. .. 436/169 |
| 5,569,608 A | 10/1996 | Sommer .................... 436/518 |
| 5,580,794 A | 12/1996 | Allen ........................ 436/169 |
| 5,604,110 A | 2/1997 | Baker et al. .............. 435/7.92 |
| 5,605,662 A | 2/1997 | Heller et al. ............... 422/68.1 |
| 5,628,890 A | 5/1997 | Carter et al. ................ 204/403 |
| 5,639,671 A | 6/1997 | Bogart et al. ............... 436/518 |
| 5,645,798 A | 7/1997 | Schreiber et al. ............. 422/58 |
| 5,654,178 A | 8/1997 | Fitzpatrick et al. ...... 435/70.21 |
| 5,658,802 A | 8/1997 | Hayes et al. ............... 436/518 |
| 5,682,884 A | 11/1997 | Hill et al. ................... 128/637 |
| 5,695,623 A | 12/1997 | Michel et al. .............. 204/403 |
| 6,066,243 A | 5/2000 | Anderson et al. |

MULTICHEMISTRY MEASURING DEVICE AND TEST STRIPS

This application claims priority from the provisional application Serial No. 60/110,331, filed Nov. 30, 1998.

CROSS-REFERENCE TO RELATED APPLICATIONS

This application is a application of an application Ser. No. 09/441,563 filed on evendate herewith, now U.S. Pat. No. 6,377,894, and entitled ANALYTE TEST INSTRUMENT HAVING IMPROVED CALIBRATION AND COMMUNICATION PROCESSES, the contents of which are incorporated herein by reference.

BACKGROUND OF THE INVENTION

1. Field of the Invention

This invention relates to measuring devices for performing assays for the accurate determination of the presence, concentration, or activity of one or more analytes in a sample applied to test strips adapted for use with the devices. The measuring devices and test strips of the invention are particularly useful in the fields of clinical chemistry, environmental testing, and chemical process control.

2. Discussion of the Art

Electrochemical measuring devices that detect the presence, concentration, or activity of one or more analytes in a solution are well known in the art. In addition, disposable electrochemical test strips adapted for use with such devices are known in the art. For example, test strips are disclosed in U.S. Pat. No. 5,628,890; strip electrodes with screen printing are disclosed in U.S. Pat. No. 5,509,410; and additional strip electrodes with screen printing are disclosed in U.S. Pat. No. 5,682,884. In such devices, a sample is applied to the test strip, and the test strip is inserted into a port on the measuring device. Such measuring devices and test strips are commercially available for home use by diabetics for the measurement of blood glucose (e.g., the PRECISION Q·I·D blood glucose testing system manufactured and sold by MEDISENSE, Inc., Waltham, Mass.). Other devices are commercially available, for use by home users or clinicians, for the electrochemical measurement of other blood analytes and parameters, such as lactate or urea. However, in the prior art, the measurement of multiple analytes or parameters in a sample typically requires the use of multiple measuring devices, each adapted for a different testing functionality, or a single measuring device in which the user must manually switch the device between different testing functionalities.

There is, therefore, a need in the art for products and methods by which a user may perform a multiplicity of different assays with a single measuring device having a multiplicity of testing functionalities, but without having to manually reconfigure or switch between different functionalities of the device, and without the need for a complex or expensive port or test strip design.

SUMMARY OF THE INVENTION

The invention provides a multichemistry measuring apparatus and diagnostic test strips which, in combination with the multichemistry measuring apparatus, provide a multichemistry diagnostic testing system. In one aspect, the invention relates to diagnostic test strips for chemical analysis of a sample. The diagnostic test strips are adapted for use in combination with a measuring apparatus having a test port. The apparatus is capable of performing a multiplicity of testing functionalities. In this aspect, the test strip comprises a support capable of releasably engaging the test port; at least one reaction area on the support for receiving the sample; and an indicator capable of interacting with the test port to select one of the multiplicity of testing functionalities of the measuring apparatus. In one embodiment, the indicator comprises one or more electrically conductive contacts capable of engaging at least two electrically conductive pins within the test port. In such an embodiment, the electrically conductive contacts close at least one circuit between the at least two electrically conductive pins within the test port. In preferred embodiments, the electrically conductive contacts comprise a material selected from: carbon, gold, silver, platinum, nickel, palladium, titanium, copper, or lead. In preferred embodiments, the electrically conductive contacts comprise an electrically conductive printable ink. In another embodiment, the indicator comprises one or more projections or depressions capable of mechanically engaging one or more pins within the test port. In such an embodiment, the mechanical displacement of at least one of the pins results in the opening or closing of at least one circuit. In another embodiment, the indicator comprises an optically detectable pattern capable of signaling to or being detected by an optical detector in the test port. In preferred embodiments, the optically detectable indicator comprises a pattern formed by a printable ink.

In another aspect, the present invention provides a test port for use in a measuring apparatus that is capable of performing a multiplicity of testing functionalities and is adapted for use in combination with a multiplicity of different types of diagnostic test strips. Each type of test strip corresponds to at least one of the testing functionalities of the apparatus, and at least some types of test strips have indicators of the testing functionality on them. In this aspect, the test port comprises a sensor capable of specifically interacting with the indicator(s) on the test strips, thereby selecting one of the multiplicity of testing functionalities corresponding to the type of test strip. In one embodiment, the indicators on the test strips are electrically conductive, and the sensor of the test port comprises a multiplicity of electrically conductive pins. In such an embodiment, at least two of the pins can be bridged by an indicator, thereby closing an electrical circuit. In another embodiment, the indicators on the test strips comprise projections or depressions, and the sensor of the port is a pin that may be physically displaced by or into the indicators, thereby opening or closing an electrical circuit. In another embodiment, the indicators comprise an optically detectable pattern, and the sensor of the port is an optical sensor.

In another aspect, the invention provides a measuring apparatus having a multiplicity of testing functionalities for chemical analysis. The apparatus is adapted for use in combination with a multiplicity of different types of test strips. Each of the types of test strips corresponds to at least one of the testing functionalities, and at least some of the types of test strips have indicators of the testing functionality on them. The apparatus includes: a test port including a sensor capable of interacting with the indicators on the test strips to select one of the multiplicity of testing functionalities; and a multiplicity of test circuitries for specifically measuring reactions on the test strips, the reactions corresponding to the multiplicity of testing functionalities.

In some embodiments, the assay may detect the presence, concentration, or activity of one or more of the following in a sample: L-amino acids, alcohols, aldehydes, ketones, urea, creatinine, xanthines, sarcosine, glucolate, pyruvate, lactate, fructosamine, methylamine, carbon monoxide, cholesterol, hemoglobin, glycated hemoglobin, microalbumin, high density lipoproteins, low density lipoproteins, and glucose.

In some embodiments, the reaction area includes one or more reagents adsorbed to the support. The reagents are capable of reacting with an analyte in the sample. In preferred embodiments, the reagent is selected from, but not limited to, one of the following: glucose oxidase, lactate dehydrogenase, peroxidase, and galactose oxidase.

In some embodiments, the test strip further comprises a multiplicity of electrically conductive testing contacts capable of transferring current between the reaction area and the measuring device. In certain of these embodiments, the testing contacts are located on a first major surface of the test strip, and the indicator contacts are located on a second major surface of the test strip. In other embodiments, the testing contacts and indicator contacts are located on the same major surface of the test strip. In preferred embodiments, the testing contacts comprise a conductive material selected from, but not limited to, carbon, gold, silver, platinum, nickel, palladium, titanium, copper, or lead.

DETAILED DESCRIPTION OF THE INVENTION

The invention provides measuring devices for performing assays for the accurate determination of the presence, concentration, or activity of one or more analytes in a sample applied to test strips adapted for use with the devices. The multichemistry measuring device and test strips of the invention have particular utility in fields including, but not limited to, clinical chemistry, chemical process control, and environmental testing. For example, the multichemistry measuring device and test strips can be used in clinical chemistry to determine the levels of particular analytes (e.g., glucose, cholesterol, urea, creatinine) in body fluids (e.g., whole blood, serum, urine), in environmental testing to determine the presence or concentration of pollutants (e.g., PCBS) or biohazards (e.g., bacteria, virus), or in chemical process control for monitoring the progress of a process by detecting the presence, concentration, or activity or various adducts, edducts,or other parameters (e.g., pH, salinity).

In particular, the present invention provides methods and products for use therewith by which a user may perform a multiplicity of different assays with a single measuring device having a multiplicity of testing functionalities, but without the need for manually reconfiguring or switching between different functionalities of the device. By eliminating the need for the user to manually set the device when changing from one test to another, the present invention provides for increased convenience and speed of use, and reduces the likelihood of human error. To achieve these ends, the invention employs a multichemistry test port that is capable of recognizing various diagnostic test strips having different testing functionalities. Each type of diagnostic test strip comprises a different indicator (or indicators) that enable the test port to differentiate it from other types of diagnostic test strips. When the user inserts the test strip into the test port, the test port will identify the corresponding functionality of the device and automatically reconfigure or switch the measuring device to the appropriate functionality.

In one embodiment, the overall system comprises an electrochemical measuring device comprising a multichemistry test port in electrical communication with a multiplicity of different testing functionalities. The test port is capable of releasably engaging various diagnostic test strips having different testing functionalities. The diagnostic test strip comprises at least two test electrodes (a reference electrode and a working electrode) and a reaction area. When a fluid sample is added to the reaction area, the sample brings the reference electrode into electrical communication with the working electrode. When a diagnostic test strip is releasably engaged in the test port, the working electrode and the reference electrode are brought into electrical communication with at least one of a multiplicity of circuits corresponding to the different testing functionalities of the measuring device. The indicators on the test strip determine which of the multiplicity of circuits corresponding to the different testing functionalities of the measuring device is activated and employed.

Diagnostic Test Strips

At minimum, the test strips of the invention comprise a support, which receives the sample and releasably engages the test port. The support bears one or more indicators that correspond to the testing functionality of the test strip. The support can be produced from materials including, but not limited to, PVC or other plastics, ceramic materials, or printed-circuit-board laminates. In preferred embodiments, the support is substantially flat and elongated with the indicators at or near a first end, and a reaction area at or near a second end.

In preferred embodiments, the assay to be performed is electrochemical in nature, and the test strip further comprises electrically conductive testing contacts in electrical communication with the reaction area and extending toward the first end. In such embodiments, the testing contacts are capable of transferring current between the reaction area and the measuring device. The testing contacts can be composed of, but are not limited to, conductive materials, such as, for example: carbon, gold, silver, platinum, nickel, palladium, titanium, copper, and lead.

In general, the reaction area in such embodiments typically comprises a conductive electrode coated with a mixture of a catalytically active enzyme and an optional mediator compound, and is preferably further coated or covered by a permeable retaining membrane. The enzyme and optional mediator compound can be coated in separate layers. When such a coated electrode is contacted with a sample containing an analyte for which the enzyme exerts a catalytic effect, the analyte of interest passes through the permeable retaining membrane and reacts with the enzyme and mediator compound (when present) to produce an activated form of the mediator compound. The activated mediator compound transfers electrons to the electrode to produce a signal, which is correlated with the concentration of the analyte. In other embodiments, a mediator compound is not necessary, and the reaction between an analyte and an enzyme produces a product (e.g., hydrogen peroxide) that is capable of transferring electrons to the electrode. Thus, in one particular embodiment, the analyte may be glucose and the catalytically active enzyme may be glucose oxidase, and the measuring device and test strips of the invention may be used to ascertain the concentration of glucose in a fluid sample such as blood. In a second particular embodiment, the analyte may be lactate and the catalytically active enzyme may be lactate dehydrogenase, and the measuring device and test strips of the invention may be used to ascertain the concentration of lactate in blood. However, in these different particular embodiments, the measuring device must employ different testing functionalities or circuitries with the different test strips. Therefore, it is vital to the proper functioning of the system that the measuring device perform the correct testing functionality when a particular type of test strip is inserted into the multichemistry test port.

As stated previously, the invention provides a multiplicity of test strips capable of performing a multiplicity of diagnostic tests, but which can be used with a single measuring device having a single test port, without the need for manual reconfiguration or switching between different testing functionalities of the device. The invention provides for indicators on the test strips, which indicators can be recognized by a sensor within the multichemistry test port in order to ascertain the testing functionality that the measuring device should perform. For the purposes of this invention, the term "indicator" refers to any pattern of information capable of being recognized by the test port, including the absence of any discernible pattern (i.e., a "null" pattern). The types of indicators employed in the present invention include, but are not limited to, mechanical, electrical, and optical indicators, as well as any combinations thereof.

In a particularly preferred embodiment, the indicators comprise electrically conductive patterns on a major surface of a test strip. In this embodiment, when the test strip releasably engages the test port, the indicator comes into contact with a plurality of electrically conductive pins in the test port. Depending upon the pattern of the indicator, a circuit between one or more pairs of the pins may be closed or "shorted" by the conductive material of the indicator. The measuring device detects which circuits, if any, are closed by insertion of the test strip, and selects the testing functionality appropriate for that type of test strip.

In an alternative embodiment, the indicator comprises a pattern of projections or bumps on a major surface of the test strip, and the test port includes a plurality of pins that can mechanically engage the indicator portion of the test strip. When inserted into the test port, the projections of the indicator may physically displace one or more of these pins. In one embodiment, the pin or pins may be displaced such that they are brought into electrical communication with one or more conductive elements, thus closing one or more circuits. In another embodiment, the pin or pins may be in electrical communication with one or more conductive elements before insertion of the test strip, and may be displaced by the indicator upon insertion into the test port, thus opening one or more circuits. The measuring device detects which circuits have been opened or closed by insertion of the test strip, and selects the testing functionality appropriate for that type of test strip. In a related embodiment, the indicator may comprise a pattern of indentations or holes (rather than projections or bumps) in the test strip. In such an embodiment, the test port includes a plurality of pins, which pins mechanically engage the indicator portion of the test strip and are displaced in the absence of a indentation or hole. Thus, pins that are brought into register with the indentations or holes fail to be displaced by the insertion of the test strip into the test port, and, just as the pattern of displacement of pins by projections conveys information, the pattern of non-displacement by indentations conveys information and serves to identify the type of test strip and its functionality.

In another embodiment, the indicator comprises an optically detectable pattern printed on a major surface of the test strip. Again, for the purposes of this invention, the absence of a printed pattern may also serve as an indicator. In one embodiment, the pattern may consist of regions that exhibit higher or lower reflectivity or absorbance, and the major surface of the test strip may serve as part of the pattern (e.g., by providing a background reflectivity or absorbance that differs from that of a pattern printed in ink). Alternatively, the indictor may comprise patterns of different colors, or may even comprise characters. In all cases, when the test strip is inserted into the test port, optical sensors within the test port recognize the pattern and cause the measuring device to select the testing functionality appropriate to that type of test strip.

Multichemistry Test Ports

In general, the multichemistry test port serves as an interface between the test strip and the measuring device. Therefore, for measuring devices performing electrochemical assays on samples on test strips, the test ports typically comprise two or more testing pins, which are in electrical communication with the measuring device. When a test strip engages the test port, the testing pins are brought into electrical communication with the test electrodes (i.e., the reference electrode and working electrode) located on the test strip. The present invention, however, provides for additional sensors within the test port, which sensors can recognize different types of test strips and cause the multichemistry measuring device to switch between different testing functionalities to select the testing functionality that is appropriate for the type of diagnostic test desired.

Thus, the test port is capable of detecting an indicator on a test strip and causing the measuring device to select from among a multiplicity of testing functionalities the functionality that is appropriate for the type of diagnostic test desired.

In a preferred embodiment, the sensor comprises a multiplicity of electrically conductive pins, which may be brought into electrical communication with electrically conductive printed patterns on a test strip when the test strip engages the test port. The electrically conductive pattern may close a circuit between one or more of the pins, or may be a "null" pattern, which does not electrically bridge any of the pins. Depending on which circuits are closed and which remain open, the measuring device selects the appropriate testing functionality to perform on the test strip that has been inserted into the test port.

In another embodiment, the sensor comprises one or more pins that may be mechanically engaged by an indicator when a test strip engages the test port. In such an embodiment, the indicator comprises a pattern of one or more projections or bumps capable of displacing one or more pins upon insertion of the test strip into the test port. Alternatively, the indicator comprises a pattern of one or more indentations or holes, which fail to displace one or more pins upon insertion of the test strip into the test port. The displacement, or non-displacement of these pins, may cause the opening or closing of one or more circuits. In these embodiments, the measuring device selects the appropriate testing functionality according to the pattern of displacement of the pins, and the resultant opening or closing of circuits.

In another embodiment, the sensor comprises one or more optical sensors capable of measuring light absorbance and reflectivity. In such an embodiment, each sensor measures the absorbance, reflectivity, or color, or identifies a character, at different portions of the indicator region when the test strip is engaged in the test port. Depending upon the readings returned by the sensors, the measuring device selects the appropriate testing functionality to perform on the test strip.

Reaction Areas and Circuitries

The chemical assays performed by the test strips and measuring devices of the present invention, along with the test strip reaction areas and associated measuring device circuitries, may be adapted or selected from any of those already known to those of skill in the art.

In preferred embodiments, the chemical assays are electrochemical assays utilizing enzyme electrodes, and the reaction area comprises a working electrode, a reference electrode, and an enzyme that reacts with the analyte to be measured. In such embodiments, the working electrode may further comprise a mediator (e.g., ferrocene) capable of transferring electrons between the enzyme-catalyzed reaction and the working electrode. In some embodiments, the reaction area further comprises a dummy electrode, in which the dummy electrode includes the mediator but not the enzyme.

In preferred embodiments, when the test strip engages the multichemistry test port, the working and reference electrodes are put in electrical communication with the measuring device. When the sample is added to the reaction area (before or after inserting the test strip in the test port), the sample bridges the two electrodes, putting them in electrical communication with each other, closing a circuit, and placing the sample in electrical communication with the measuring device. In some embodiments, one of the testing functionalities of the measuring device measures current through this circuit or a change in voltage potential. In other embodiments, one of the testing functionalities of the measuring device applies current to this circuit and measures resistance. The use of such systems to determine presence and concentration of analyte is discussed in, for example, U.S. Pat. No. 4,545,382, and U.S. Pat. No. 4,711,245. A sensor system that detects current that is representative of a compound in a liquid mixture featuring a test strip adapted for releasable engagement to signal readout circuitry is discussed in U.S. Pat. No. 5,509,410.

In preferred embodiments, the invention is used in clinical chemistry to determine the concentrations of several different analytes in a patient's blood. In particular embodiments, the invention may be used to determine, for example, a patient's blood glucose level, blood lactose level, and blood carbon monoxide level in quick succession. In these embodiments, one or more assays will require one or more different types of test strips, which, in turn, require different testing functionalities to be utilized by the measuring device with the different types of test strips. More than one assay may, of course, be conducted with a single test strip. Because each type of test strip of the present invention has an indicator which selects the correct testing functionality, no human intervention is required to select the correct testing functionality for the different assays.

In other embodiments, the invention can be used in chemical process control to ensure that the concentrations of various reactants or products, or other chemical reaction parameters such as pH or salinity, are within certain predefined tolerances at various stages of the process.

In other embodiments, the invention can be used in environmental testing. In particular embodiments, the invention can be used to test water quality. In one further embodiment, the invention can be used to detect the presence and amount of various pollutants such as sulfuric acid in rainwater. In other embodiments, the invention can be used to detect the presence and amount of various pollutants in oceans, lakes, ponds, streams, and rivers. In yet other embodiments, the invention can be used to measure the amounts of certain analytes such as chlorine in a swimming pool.

EXAMPLES

Differentiating Two Types of Test Strips

In one embodiment, the multichemistry measuring device is capable of performing two separate electrochemical assays for measuring two different analytes, for example, glucose and lactate, present in a blood sample. Accordingly, the multichemistry test port is capable of recognizing two different types of test strips. The first type of test strip is capable of assaying for glucose and has glucose oxidase incorporated into its working electrode. The second type of test strip is capable of assaying for lactate and has lactate dehydrogenase incorporated into its working electrode. Each type of test strip requires a unique electrochemical protocol that cannot be used with the other type of test strip.

The multichemistry test port has two electrically conductive indicator contacts that contact the bottom major surface of a test strip when the test strip is releasably engaged in the test port. The test strip is elongate and has a top major surface and a bottom major surface. The test strip for testing lactate has an indicator comprising a pattern made from an electrically conductive ink printed on the bottom major surface of the test strip. When a test strip for testing lactate is releasably engaged in the multichemistry test port, the electrically conductive indicator closes a circuit between the two electrically conductive indicator contacts, causing the multichemistry measuring device to perform an electrochemical assay for lactate. Conversely, the test strip for testing glucose does not possess an electrically conductive indicator capable of closing the circuit such that, when a test strip for testing glucose is releasably engaged in the multichemistry testing port, the circuit between the two electrically conductive indicator contacts remains open. When the circuit between the multichemistry test port's two electrically conductive indicator contacts remains open, the multichemistry measuring device performs an electrochemical assay for glucose.

Differentiating Five Types of Test Strips

In the previous example, a test port having two electrically conductive pins allowed for recognition of two alternative types of test strips having different functionalities. In this example, the use of three electrically conductive pins allows for recognition of five different types of test strips having different functionalities. As in the previous example, the test strip is elongate and has a top major surface and a bottom major surface. A pattern of electrically conductive ink is printed on the bottom major surface of the test strip. The test port has three electrically conductive pins that come into contact with the printed pattern on the bottom major surface of the test strip when the test strip is releasably engaged in the test port.

The possible configurations of the printed pattern are illustrated in FIG. 1. In configuration A, there is no electrically conductive material present, and the indicator is "null." Thus, none of the circuits among the pins are closed by engaging the test strip within the test port. In configuration B, the electrically conductive indicator pattern shorts pins 1 and 2, thereby closing the circuit between these pins. In configuration C, the electrically conductive indicator pattern shorts pins 1 and 3, thereby closing the circuit between these pins. In configuration D, the electrically conductive indicator pattern shorts pins 2 and 3, thereby closing the circuit between these pins. Finally, in configuration E, the circuits between all three pins are closed.

In general, a test port with N electrically conductive pins can recognize $2^N-N$ different configurations of indicators.

Figure 4:
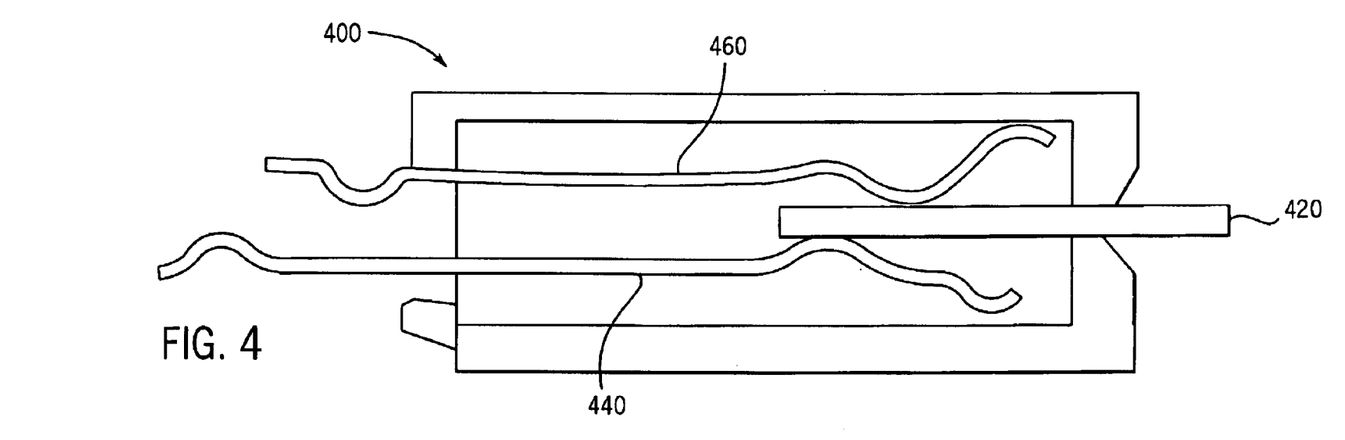
FIG. 4 depicts a side cut-away view of a test port and test strip in which the indicators are electrically conductive.

FIG. 4 depicts a cross section of a side view of a test port 400 engaged with a test strip 420 having electrically conductive indicators. The test port 400 includes electrically conductive pins 440 that are brought into electrical communication with the bottom major surface of test strip 420 when the test strip 420 is releasably engaged in the test port 400. The test port 400 also includes assay electrodes 460 that are brought into electrical communication with the top major surface of the test strip 420 when the test strip 420 is releasably engaged in the test port 400.

Mechanically Detectable Indicator Patterns

Figure 1A:
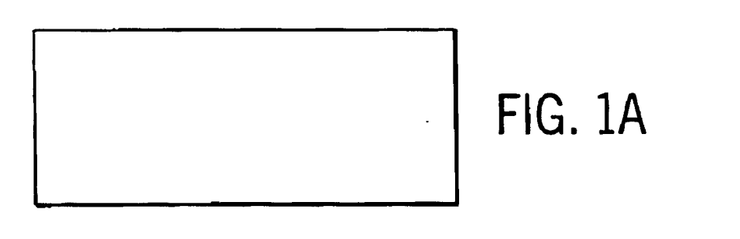
FIG. 1 depicts possible configurations of electrically conductive indicators for five different types of test strips, adapted for use with a test port having three pins.
Figure 1B:
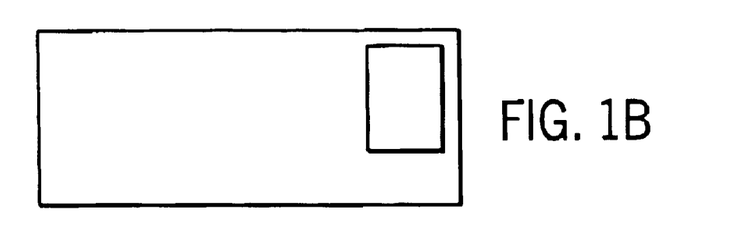
Figure 1C:
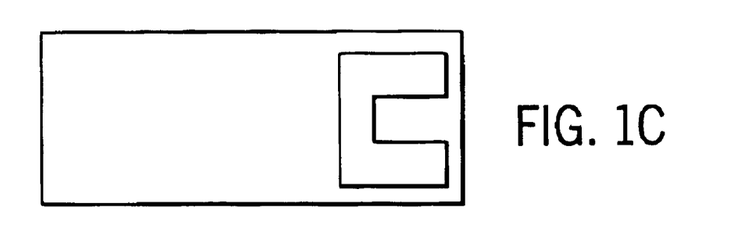
Figure 1D:
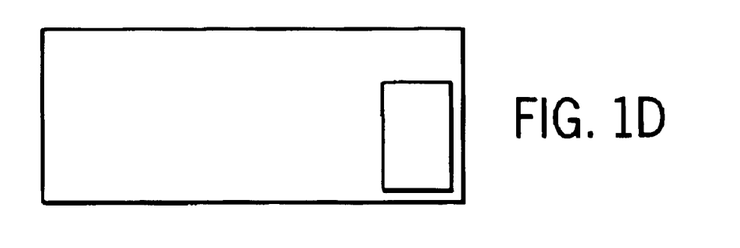
Figure 1E:
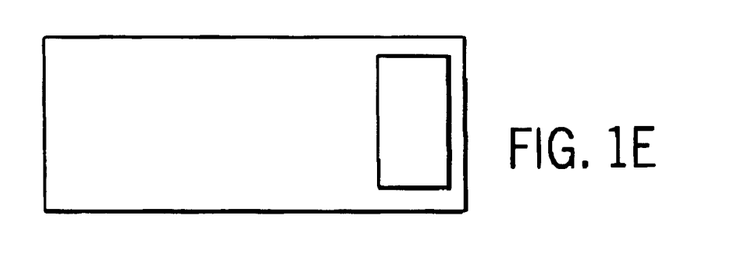
Figure 2A:
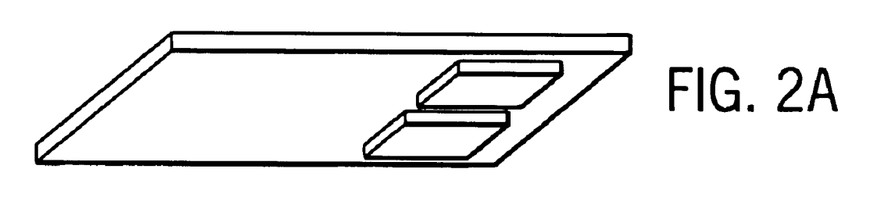
FIG. 2 depicts possible configurations of mechanical indicators for four different types of test strips, adapted for use with a test port having two pins.
Figure 2B:
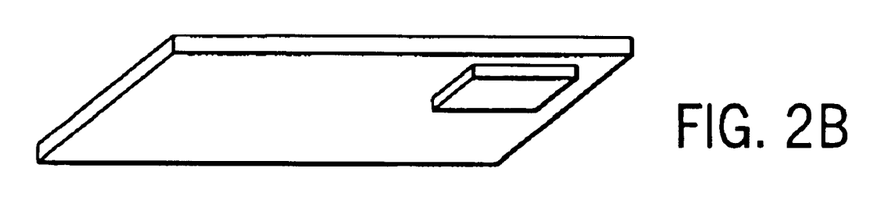
Figure 2C:
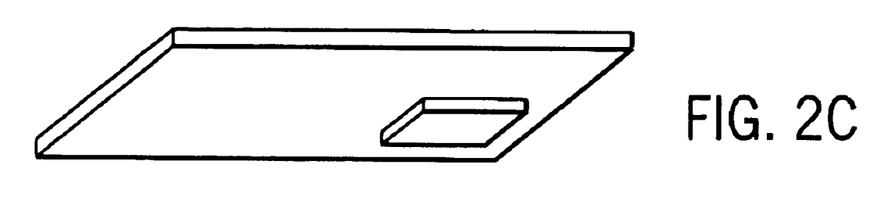
Figure 2D:
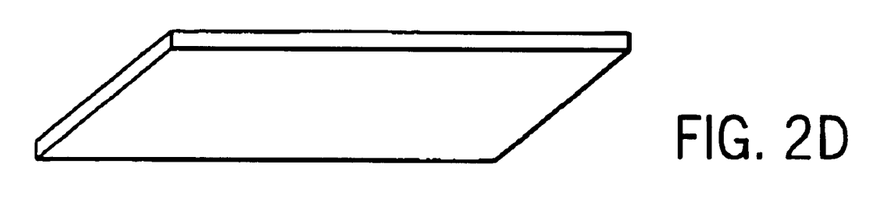
Figure 3A:
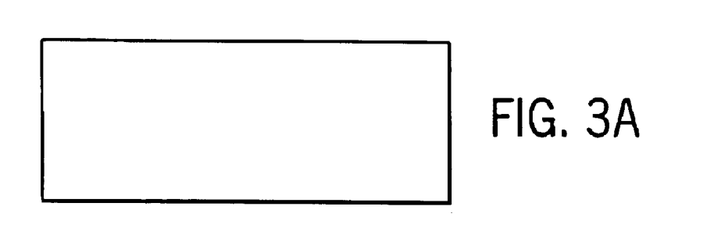
FIG. 3 depicts possible configurations of optically detectable indicators for four different types of test strip, adapted for use with a test port detecting optical characteristics at two locations.
Figure 3B:
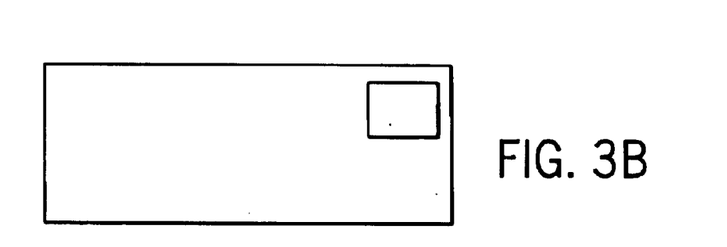
Figure 3C:
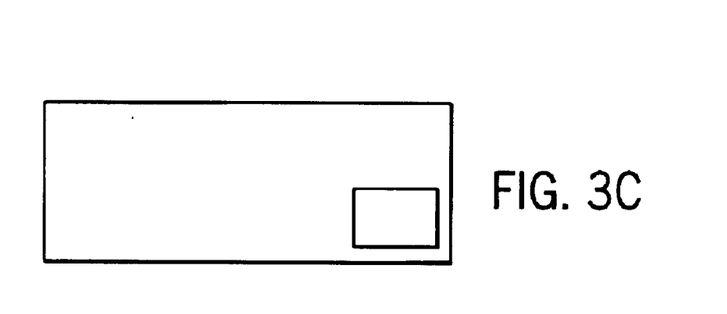
Figure 3D:
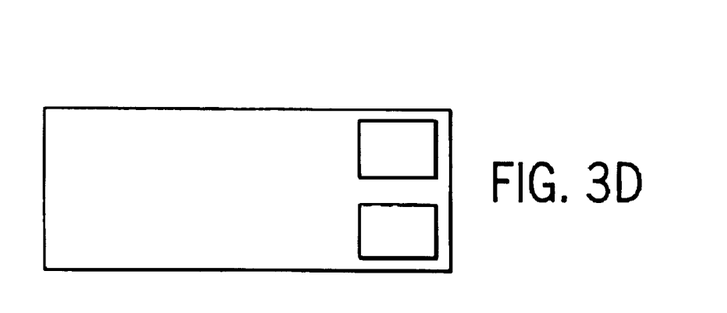

In this example, the test strip is elongate and has a top major surface and a bottom major surface. The test strip contains an indicator comprising zero or more projections on the bottom major surface thereof. The projection(s), if any, mechanically engage at least one pin in the test port. In the embodiment illustrated in FIGS. 2a–2d, the indicator pattern is determined by the presence or absence of projections in two specific locations. Upon insertion of the test strip into the test port, the projection(s) mechanically engage a sensor comprising two pins. In FIG. 2a, the indicator comprises two projections, which displace both pins. In FIG. 2b, the indicator comprises only a first projection, with the second projection is absent, resulting in only the first pin being displaced. In FIG. 2c, the indicator comprises only a second projection, with the first projection absent, resulting in only the second pin being displaced. In FIG. 2d, both projections are absent and neither pin is displaced upon insertion of the test strip into the test port.

In general, a test port that can detect projections or depressions at N spots can recognize $2^N$ different indicators.

Figure 5:
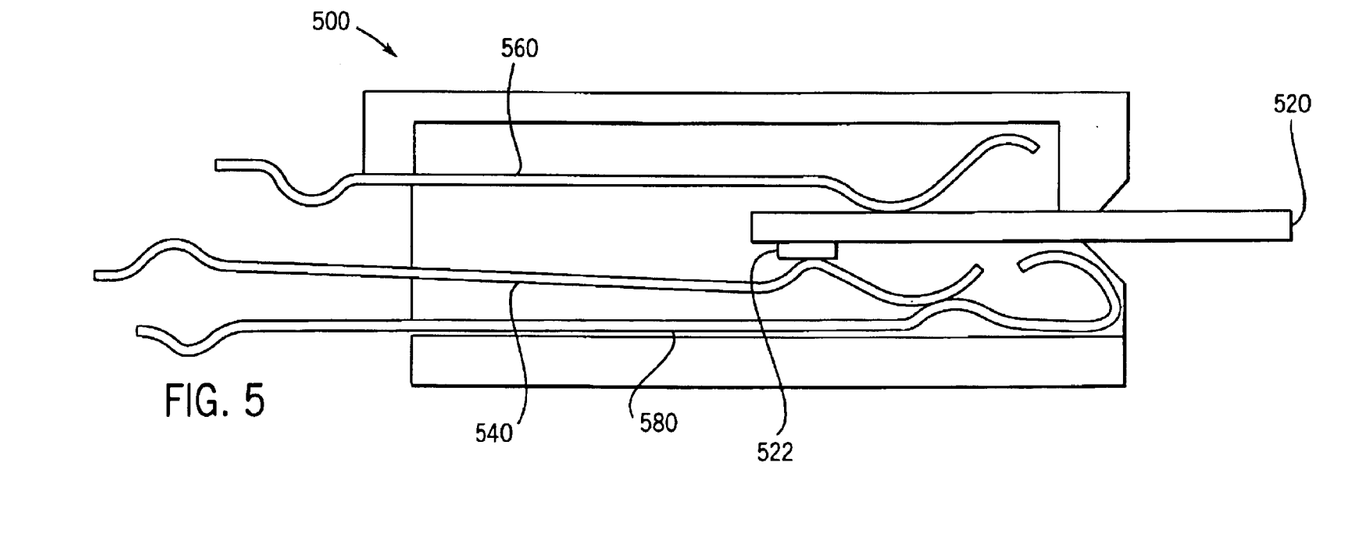
FIG. 5 depicts a side cut-away view of a test port and test strip in which the indicators are mechanical.

FIG. 5 depicts a cross section of a side view of a test port 500 engaged with a test strip 520 having electrically conductive indicators. The test port 500 includes flexible pins 540 that can be biased into electrical communication with relatively static pins 580 by an indicator 522 on the bottom major surface of the test strip 520 when the test strip 520 is releasably engaged in the test port 500. The test port 500 also includes assay electrodes 560 that are brought into electrical communication with the top major surface of the test strip 520 when the test strip 520 is releasably engaged in the test port 500.

Optically Detectable Indicator Patterns

As in the previous examples, the test strip is elongate and has a top major surface and a bottom major surface. A printed pattern is on the bottom major surface of the test strip. In this example, the test port has two optical sensors capable of detecting the presence or absence of a printed pattern at two different locations on the bottom major surface of the test strip by measuring absorbance and/or reflectance of light at those locations. As illustrated in FIG. 3, this example allows for four (4) different configurations: (a) both locations "off", (b) first location "on" and second location "off", (c) first location "off" and second location "on", and (d) both locations "on".

In general, a test port that can optically detect absorbance and/or reflectance at N locations can recognize $2^N$ different configurations of indicators.

Resistance-based Indicators

As in the previous examples, the test strip is elongate and has a top major surface and a bottom major surface. An indicator is on the bottom major surface of the test strip. In this example, the test port has two electrically conductive pins, which are bridged by the bottom major surface of the test strip when the test strip is releasably engaged in the test port. The measuring device is capable of measuring the resistance across the pins. The resistance measured can serve to indicate the type of test strip being used. If the support material is non-conductive, the lack of an additional indicator material can serve as a "null" indicator.

In general, a test port that measures resistance can recognize an arbitrarily large number of different indicators. The test port is limited only by its capacity to distinguish between gradations in resistance.

Equivalents

The invention may be embodied in other specific forms without departing from the spirit or essential characteristics thereof. The foregoing embodiments are therefore to be considered in all respects illustrative rather than limiting on the invention described herein. The scope of the invention is therefore indicated by the appended claims rather than by the foregoing description, and all changes which come within the meaning and range of equivalency of the claims are therefor intended to be embraced thereby.

What is claimed is:

1. A test strip for chemical analysis of a sample, adapted for use in combination with a measuring device having a test port and capable of performing a multiplicity of testing functionalities, said test strip comprising:

(a) a support capable of releasably engaging said test port;

(b) at least one reaction area on said support for receiving said sample; and (c) an indicator capable of interacting with said test port to select only one of said multiplicity of testing functionalities of said measuring device, wherein said indicator comprises at least one electrically conductive indicator contact capable of engaging at least two electrically conductive pins within said test port to thereby select only one of said multiplicity of testing functionalities of said measuring device.

2. The test strip of claim 1, wherein said indicator contacts comprise a material selected from the group consisting of carbon, gold, silver, platinum, nickel, palladium, titanium, copper, and lead.

3. The test strip of claim 2, wherein said material is a printable ink.

4. The test strip of claim 1, wherein said sample is a bodily fluid.

5. The test strip of claim 1, wherein said chemical analysis comprises measuring in said sample the concentration of a compound selected from the group consisting of L-amino acids, alcohols, aldehydes, ketones, urea, creatinine, xanthines, sarcosine, glucolate, pyruvate, lactate, fructosamine, methylamine, carbon monoxide, cholesterol, hemoglobin, glycated hemoglobin, microalbumin, high density lipoproteins, and low density lipoproteins.

6. The test strip of claim 1, wherein said compound is glucose.

7. The test strip of claim 1, wherein said reaction area comprises at least one reagent adsorbed to said support, said at least one reagent capable of reacting with a compound in said sample.

8. The test strip of claim 7, wherein said at least one reagent is selected from the group consisting of glucose oxidase, lactate dehydrogenase, peroxidase, and galactose oxidase.

9. The test strip of claim 1, further comprising a multiplicity of electrically conductive testing contacts capable of transferring current between said reaction area and said measuring device.

10. The test strip of claim 9, wherein said testing contacts comprise a material selected from the group consisting of carbon, gold, silver, platinum, nickel, palladium, titanium, copper and lead.

11. The test strip of claim 10, wherein said material is a printable ink.

12. The test strip of claim 9, wherein said testing contacts are located on a first major surface of said test strip and said indicator is located on a second major surface of said test strip.

13. The test strip of claim 9, wherein said testing contacts and said indicator are located on the same surface of said test strip.

14. A test strip for chemical analysis of a sample, adapted for use in combination with a measuring device having a test port and capable of performing a multiplicity of testing functionalities, said test strip comprising:
(a) a support capable of releasably engaging said test port;
(b) at least one reaction area on said support for receiving said sample; and
(c) an indicator capable of interacting with said test port to select only one of said multiplicity of testing functionalities of said measuring device, wherein said indicator comprises at least one projection on said support, said at least one projection capable of mechanically engaging at least one pin within said test port to thereby select only one of said multiplicity of testing functionalities of said measuring device.

15. The test strip of claim 14, wherein said at least one projection displaces said at least one pin.

16. The test strip of claim 14, wherein said sample is a bodily fluid.

17. The test strip of claim 14, wherein said chemical analysis comprises measuring in said sample the concentration of a compound selected from the group consisting of L-amino acids, alcohols, aldehydes, ketones, urea, creatinine, xanthines, sarcosine, glucolate, pyruvate, lactate, fructosamine, methylamine, carbon monoxide, cholesterol, hemoglobin, glycated hemoglobin, microalbumin, high density lipoproteins, and low density lipoproteins.

18. The test strip of claim 14, wherein said compound is glucose.

19. The test strip of claim 14, wherein said reaction area comprises at least one reagent adsorbed to said support, said at least one reagent capable of reacting with a compound in said sample.

20. The test strip of claim 19, wherein said at least one reagent is selected from the group consisting of glucose oxidase, lactate dehydrogenase, peroxidase, and galactose oxidase.

21. The test strip of claim 14, further comprising a multiplicity of electrically conductive testing contacts capable of transferring current between said reaction area and said measuring device.

22. The test strip of claim 21, wherein said testing contacts comprise a material selected from the group consisting of carbon, gold, silver, platinum, nickel, palladium, titanium, copper and lead.

23. The test strip of claim 22, wherein said material is a printable ink.

24. The test strip of claim 21, wherein said testing contacts are located on a first major surface of said test strip and said indicator is located on a second major surface of said test strip.

25. The test strip of claim 21, wherein said testing contacts and said indicator are located on the same major surface of said test strip.

26. A test strip for chemical analysis of a sample, adapted for use in combination with a measuring device having a test port and capable of performing a multiplicity of testing functionalities, said test strip comprising:
(a) a support capable of releasably engaging said test port;
(b) at least one reaction area on said support for receiving said sample; and
(c) an indicator capable of interacting with said test port to select only one of said multiplicity of testing functionalities of said measuring device, wherein said indicator comprises at least one depression on said support, said at least one depression capable of mechanically engaging at least one pin within said test port to thereby select only one of said multiplicity of testing functionalities of said measuring device.

27. The strip of claim 26, wherein at least one of said pins can be displaced into at least one of said depressions.

28. The test strip of claim 26, wherein said at least one depression defines at least one hole.

29. The test strip of claim 26, wherein said sample is a bodily fluid.

30. The test strip of claim 29, wherein said chemical analysis comprises measuring in said sample the concentration of a compound selected from the group consisting of L-amino acids, alcohols, aldehydes, ketones, urea, creatinine, xanthines, sarcosine, glucolate, pyruvate, lactate, fructosamine, methylamine, carbon monoxide, cholesterol, hemoglobin, glycated hemoglobin, microalbumin, high density lipoproteins, and low density lipoproteins.

31. The test strip of claim 26, wherein said compound is glucose.

32. The test strip of claim 26, wherein said reaction area comprises at least one reagent adsorbed to said support, said at least one reagent capable of reacting with a compound in said sample.

33. The test strip of claim 32, wherein said at least one reagent is selected from the group consisting of glucose oxidase, lactate dehydrogenase, peroxidase, and galactose oxidase.

34. The test strip of claim 26, further comprising a multiplicity of electrically conductive testing contacts capable of transferring current between said reaction area and said measuring device.

35. The test strip of claim 34, wherein said testing contacts comprise a material selected from the group consisting of carbon, gold, silver, platinum, nickel, palladium, titanium, copper and lead.

36. The test strip of claim 35, wherein said material is a printable ink.

37. The test strip of claim 34, wherein said testing contacts are located on a first major surface of said test strip and said indicator is located on a second major surface of said test strip.

38. The test strip of claim 34, wherein said testing contacts and said indicator are located on the same major surface of said test strip.

39. A test strip for chemical analysis of a sample, adapted for use in combination with a measuring device having a test port and capable of performing a multiplicity of testing functionalities, said test strip comprising:
    (a) a support capable of releasably engaging said test port;
    (b) at least one reaction area on said support for receiving said sample; and
    (c) an indicator capable of interacting with said test port to select only one of said multiplicity of testing functionalities of said measuring device, wherein said indicator comprises an optically detectable pattern capable of signaling or being detected by an optical detector in said test port to thereby select only one of said multiplicity of testing functionalities of said measuring device.

40. The test strip of claim 39, wherein said sample is a bodily fluid.

41. The test strip of claim 39, wherein said chemical analysis comprises measuring in said sample the concentration of a compound selected from the group consisting of L-amino acids, alcohols, aldehydes, ketones, urea, creatinine, xanthines, sarcosine, glucolate, pyruvate, lactate, fructosamine, methylamine, carbon monoxide, cholesterol, hemoglobin, glycated hemoglobin, microalbumin, high density lipoproteins, and low density lipoproteins.

42. The test strip of claim 39, wherein said compound is glucose.

43. The test strip of claim 39, wherein said reaction area comprises at least one reagent adsorbed to said support, said at least one reagent capable of reacting with a compound in said simple.

44. The test strip of claim 43, wherein said at least one reagent is selected from the group consisting of glucose oxidase, lactate dehydrogenase, peroxidase, and galactose oxidase.

45. The test strip of claim 39, further comprising a multiplicity of electrically conductive testing contacts capable of transferring current between said reaction area and said measuring device.

46. The test strip of claim 45, wherein said testing contacts comprise a material selected from the group consisting of carbon, gold, silver, platinum, nickel, palladium, titanium, copper and lead.

47. The test strip of claim 46, wherein said material is a printable ink.

48. The test strip of claim 45, wherein said testing contacts are located on a first major surface of said test strip and said indicator is located on a second major surface of said test strip.

49. The test strip of claim 45, wherein said testing contacts and said indicator are located on the same major surface of said test strip.

50. A test port for use in a measuring device capable of performing a multiplicity of testing functionalities and adapted for use with the test strip of claim 1, said test port comprising at least two electrically conductive pins, said at least two electrically conductive pins capable of specifically interacting with said at least one electrically conductive indicator contact on said test strip to thereby select only one of said multiplicity of testing functionalities of said measuring device.

51. The test port of claim 50, wherein at least two of said electrically conductive pins can be bridged by said at least one electrically conductive indicator contact, thereby closing an electrical circuit.

52. A test port for use in a measuring device capable of performing a multiplicity of testing functionalities and adapted for use with the test strip of claim 14, wherein said test port comprises at least one pin that can be mechanically engaged by said indicator on said test strip, thereby either closing an electrical circuit or opening an electrical circuit.

53. A test port for use in a measuring device capable of performing a multiplicity of testing functionalities and adapted for use with the test strip of claim 26, wherein said test port comprises a pattern of at least one indentation or hole, wherein said at least one indentation or hole fails to displace at least one pin of said test strip upon insertion of said test strip into said test port to thereby select only one of said multiplicity of testing functionalities of said measuring device.

54. A test port for use in a measuring device capable of performing a multiplicity of testing functionalities and adapted for use with the test strip of claim 39, wherein said test port comprises at least one optical sensor capable of measuring light absorbance, reflectivity, color, or a character.

55. A measuring device having a multiplicity of testing functionalities for chemical analysis, adapted for use with the test strip of claim 1, said device comprising:
    (a) a test port comprising at least two electrically conductive pins, said at least two electrically conductive pins capable of specifically interacting with said at least one electrically conductive indicator contact on said test strip to thereby select only one of said multiplicity of testing functionalities of said measuring device; and
    (b) a multiplicity of test circuitries for specifically measuring reactions on said test strip, said multiplicity of said test circuitries corresponding to said multiplicity of testing functionalities.

56. A measuring device having a multiplicity of testing functionalities for chemical analysis, adapted for use with the test strip of claim 4, said device comprising:
    (a) a test port comprising at least one pin that can be mechanically engaged by said indicator on said test strip, thereby either closing an electrical circuit or opening an electrical circuit; and
    (b) a multiplicity of test circuitries for specifically measuring reactions on said test strip, said multiplicity of said test circuitries corresponding to said multiplicity of testing functionalities.

57. A measuring device having a multiplicity of testing functionalities for chemical analysis, adapted for use with the test strip of claim 26, said device comprising:
    (a) a test port comprising a pattern of at least one indentation or hole, wherein said at least one indentation or hole fails to displace at least one pin of said test strip upon insertion of said test strip into said test port to thereby select only one of said multiplicity of testing functionalities of said measuring device; and
    (b) a multiplicity of test circuitries for specifically measuring reactions on said test strip, said multiplicity of said test circuitries corresponding to said multiplicity of testing functionalities.

58. A measuring device having a multiplicity of testing functionalities for chemical analysis, adapted for use with the test strip of claim 39, said device comprising:

(a) a test port comprising at least one optical sensor capable of measuring light absorbance, reflectivity, color, or a character; and (b) a multiplicity of test circuitries for specifically measuring reactions on said test trip, said multiplicity of said test circuitries corresponding to said multiplicity of testing functionalities.

* * * * *